(12) United States Patent
Spoonhower et al.

(10) Patent No.: US 7,057,639 B2
(45) Date of Patent: Jun. 6, 2006

(54) INTRA-ORAL CAMERA WITH INTEGRAL DISPLAY

(75) Inventors: John P. Spoonhower, Webster, NY (US); John R. Squilla, Rochester, NY (US); John T. Boland, Fairport, NY (US)

(73) Assignee: Eastman Kodak Company, Rochester, NY (US)

( * ) Notice: Subject to any disclaimer, the term of this patent is extended or adjusted under 35 U.S.C. 154(b) by 590 days.

(21) Appl. No.: 09/796,239

(22) Filed: Feb. 28, 2001

(65) Prior Publication Data

US 2002/0118279 A1    Aug. 29, 2002

(51) Int. Cl.
*H04N 7/18*     (2006.01)
(52) U.S. Cl. .......................................... 348/66; 348/65
(58) Field of Classification Search ............ 348/65–77; 600/109, 172, 101, 118; 604/167, 264–265
See application file for complete search history.

(56) References Cited

U.S. PATENT DOCUMENTS

| | | | | |
|---|---|---|---|---|
| 4,742,819 A | | 5/1988 | George ........................... 128/6 |
| 5,134,469 A | | 7/1992 | Uchimura ..................... 358/98 |
| 5,363,838 A | | 11/1994 | George ........................... 128/6 |
| 5,527,261 A | * | 6/1996 | Monroe et al. ............. 600/109 |
| 5,766,006 A | | 6/1998 | Murljacic ..................... 433/26 |
| 5,820,606 A | * | 10/1998 | Davis et al. ................ 604/256 |
| 5,827,178 A | | 10/1998 | Berall ......................... 600/185 |
| 5,877,819 A | * | 3/1999 | Branson ..................... 348/701 |
| 5,880,826 A | * | 3/1999 | Jung et al. ..................... 356/73 |
| 6,106,457 A | | 8/2000 | Perkins et al. |
| 6,123,437 A | * | 9/2000 | Holmes ....................... 362/372 |
| 6,129,553 A | | 10/2000 | Tanaka ........................ 434/263 |
| 6,132,211 A | | 10/2000 | Peithman |
| 6,190,309 B1 | | 2/2001 | Ooshima et al. |
| 6,224,542 B1 | * | 5/2001 | Chang et al. ............... 600/109 |
| 6,761,561 B1 | | 7/2004 | Mandelkern et al. |
| 2002/0067407 A1 | | 6/2002 | Cooper |
| 2002/0067408 A1 | | 6/2002 | Adair et al. |

OTHER PUBLICATIONS

"Using a Digital Camera for Colorimetry of Human Teeth" by Wenchen Wu, Jan P. Allebach, and Mostafa Analoui. IS&T's 1998 PICS Conference, pp. 37-42.

(Continued)

*Primary Examiner*—Andy Rao
(74) *Attorney, Agent, or Firm*—David M. Woods

(57) ABSTRACT

A portable intra-oral capture and display system includes: (a) a handpiece elongated for insertion into an oral cavity, said handpiece including a light emitter on a distal end thereof for illuminating an object in the cavity and an image sensor for capturing an image of the object and generating an image signal therefrom; (b) a portable, hand-cradled base containing in a single integral enclosure a light source for generating light, electronics for processing the image for display, a display monitor for displaying the image, a storage for storing the image, thereby providing a stored image for subsequent review and access, and an interface for transferring the stored image to a peripheral device; and (c) an optical connection for transmitting the light from the base to the light emitter in the camera, and an electrical connection for communicating the image signal from the image sensor in the camera to the processor in the base.

25 Claims, 6 Drawing Sheets

OTHER PUBLICATIONS

"Imaging Colorimetry Using a Digital Camera" by Wenchen Wu, Jan P. Allebach, and Mostafa Analoui. The Seventh Color Imaging Conference: Color Science, Systems, and Applications, pp. 15-20.

"The Reveal Imaging Platform: A System of Options" Reveal™, Welch Allyn.

Casio EV660. Casio 3" Color Active Matrix Handheld TV.

* cited by examiner

INTRA-ORAL CAMERA WITH INTEGRAL DISPLAY

FIELD OF THE INVENTION

The present invention relates to intra-oral imaging systems for dental applications, and particularly to an intra-oral camera system that is used by a dental practitioner to display images of objects in the mouth.

BACKGROUND OF THE INVENTION

Electronic handheld cameras configured with intra-oral imaging optics are used for capturing images of the inside of a patient's mouth. The camera typically has an elongated body that contains an image sensor and optics. The optics and sensor are designed for capturing images of the inside of the mouth when the distal or viewing end of the camera is inserted into the patient's mouth. Wires carrying electronic signals typically connect the image sensor to the proximal end of the camera where a communication interface is provided to an image processing system or display monitor that allows manipulation and display of the images. By viewing the displayed images, a diagnosis can be made and appropriate treatment prescribed.

For illuminating the inside of the mouth, a fiber optic cable typically is used to transmit light to the viewing end of the camera. The light is generated by a high intensity light source such as a lamp or bulb typically held in a light box. In a typical embodiment, such as shown in U.S. Pat. No. 6,132,211, the fiber optic cable terminates in a connector that plugs into a power source housing that also includes the light source. Preferably, the housing for the power supply and the light source is supported on a countertop or on a post in the dental operatory room. In other words, the housing is basically immovable and portability is provided by having the portable handpiece removable from the housing. According to the '211 patent, this design is chosen so that any number of operatories having a power source base and display may be serviced by a single handpiece system.

In a typical installation, the housing containing the power supply and the light box includes a communications interface to an external image processing system or display monitor. This leads to various placements of the processor and monitor. For instance, in the Reveal® Imaging Platform sold by Welch Allyn® the monitor is mounted on top of the housing, which makes the whole assembly virtually unmovable. Consequently, similar to what was described above in connection with the '211 patent, in the Reveal® Imaging Platform the handpiece is plugged into a receptacle on the housing.

The use of intra-oral cameras among dental practitioners is well known. Besides their use in the diagnosis of dental and oral disease, they are used as well in providing a visual record of the condition of the patient. It is frequently the case that a dentist, orthodontist, or the like, may have multiple operatories where the use of such a camera is desirable. Current camera systems require either the use of an attached computer system and video monitor, or a separate monitor for the display of images. Thus the practitioner is required to either purchase multiple camera systems or display capabilities for each operatory, as such display systems are rather large and bulky.

In many cases, a dentist desires to produce images of the interior of a patient's mouth in order to provide both a diagnosis of dental and oral disease as well as to provide a visual record of the condition of the patient. This process becomes cumbersome, costly, and inconvenient, as current camera systems are not designed for portability. What is needed is a truly portable camera system that would incorporate an integral display and provide advantages over the current state-of-the-art. Such a camera could incorporate wireless or other means to transmit the image data to a centrally located data storage and printing system.

SUMMARY OF THE INVENTION

It is an object of the present invention to provide an intra-oral camera system with improved portability.

It is a further object of the invention to provide an improved ability of the camera system to communicate with peripherals while preserving its portability.

The present invention is directed to overcoming one or more of the problems set forth above. Briefly summarized, according to one aspect of the present invention, the invention resides in a portable intra-oral capture and display system comprising: (a) a handpiece elongated for insertion into an oral cavity, wherein the handpiece includes a light emitter on a distal end thereof for illuminating an object in the cavity and an image sensor for capturing an image of the object and generating an image signal therefrom; (b) a portable, hand-cradled base tethered to the handpiece, wherein the base contains in a single integral enclosure a light source for generating light, electronics for processing the image for display, a display monitor for displaying the image, a storage for storing the image, thereby providing a stored image for subsequent review and access, and an interface for transferring the stored image to a peripheral device; and (c) an optical connection for transmitting the light from the base to the light emitter in the camera, and an electrical connection for communicating the image signal from the image sensor in the camera to the processor in the base.

In a further aspect of the invention, the capture and display system includes both a high quality image display along with means to transfer image data to a physically separate and distinct data storage in a peripheral device, such as a larger monitor, a printer or a computer. The means to transfer image data may comprise, for example: (a) wireless RF or microwave transceiver technology, (b) wireless IR technology, or (c) a physically small memory device, such as a flash RAM card, that is easily removed from the camera part of the system and subsequently plugged into the peripheral device.

The advantage of the present invention lies in the integration of the display into the camera system. This integration enables the practitioner to view the results of image recording in close proximity to the capture location, and conveniently display the captured image(s) either for the practitioner's or patient's benefit. Such viewing occurs without the requirement of producing a physical print of the image. Integration of the display removes the requirement on the dentist to move a large bulky system (a video monitor and/or attached computer) from one operating room to the next. Alternatively, the requirement that the dentist purchase multiple such systems is eliminated.

These and other aspects, objects, features and advantages of the present invention will be more clearly understood and appreciated from a review of the following detailed description of the preferred embodiments and appended claims, and by reference to the accompanying drawings.

DESCRIPTION OF THE PREFERRED EMBODIMENTS

Because intra-oral cameras employing electronic sensors are well known, the present description will be directed in particular to elements forming part of, or cooperating more directly with, apparatus in accordance with the present invention. Elements not specifically shown or described herein may be selected from those known in the art. Certain aspects of the embodiments to be described may be provided in software. Given the system as shown and described according to the invention in the following materials, software not specifically shown, described or suggested herein that is useful for implementation of the invention is conventional and within the ordinary skill in such arts.

Figure 1:
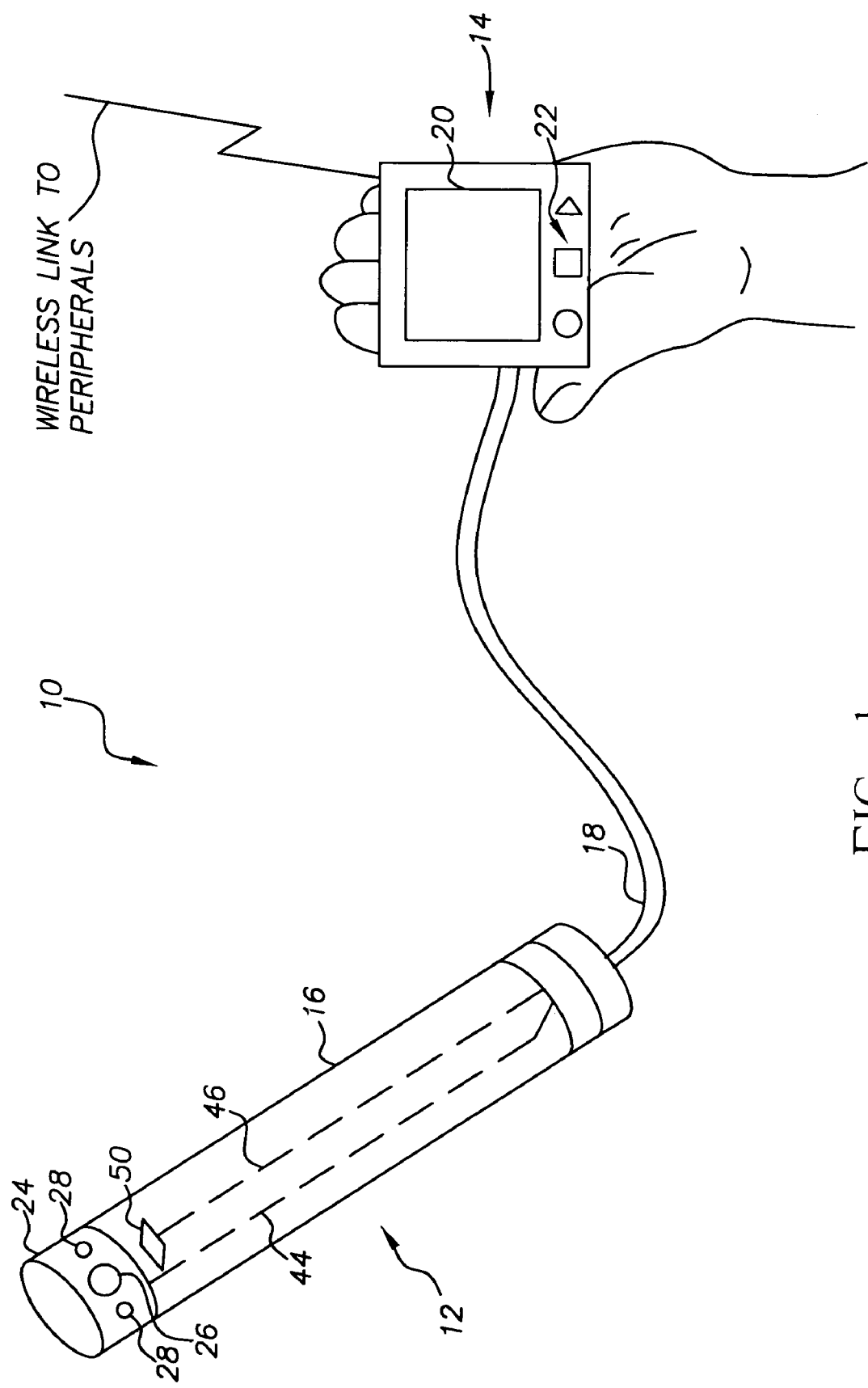
FIG. 1 shows an intra-oral camera and display system according to the invention.

Referring first to FIG. 1, an intra-oral dental camera system 10 includes a portable dental camera 12 and a power source, illumination source and a display unit integrally located in a portable enclosure (hereinafter referred to as the integral base 14) tethered to the camera 12. The camera 12 and the integral base 14 thus constitute, in the terms of this invention, an intra-oral camera with integral display. The dental camera 12 includes a handpiece 16 and a cable 18 connecting the dental camera 12 to the integral base 14. As shown for illustrative purposes in FIG. 1, the integral base 14 can be easily cradled in a hand, and includes a display monitor 20 that can be easily hand positioned relative to the dentist's and/or patient's line of sight. A set of user controls 22 are provided on the integral base 14 that can be easily hand-navigated for controlling the illumination and the images displayed on the monitor, as well as communicating with peripheral devices. The handpiece 16 supports a removable lens unit 24 that includes a lens 26 and light emitting apertures 28. The handpiece 16 is generally elongated and cylindrical with a central axis. The lens 26 is positioned to receive light impinging on the handpiece in a direction substantially perpendicular and normal to the central axis of the handpiece.

Figure 2:
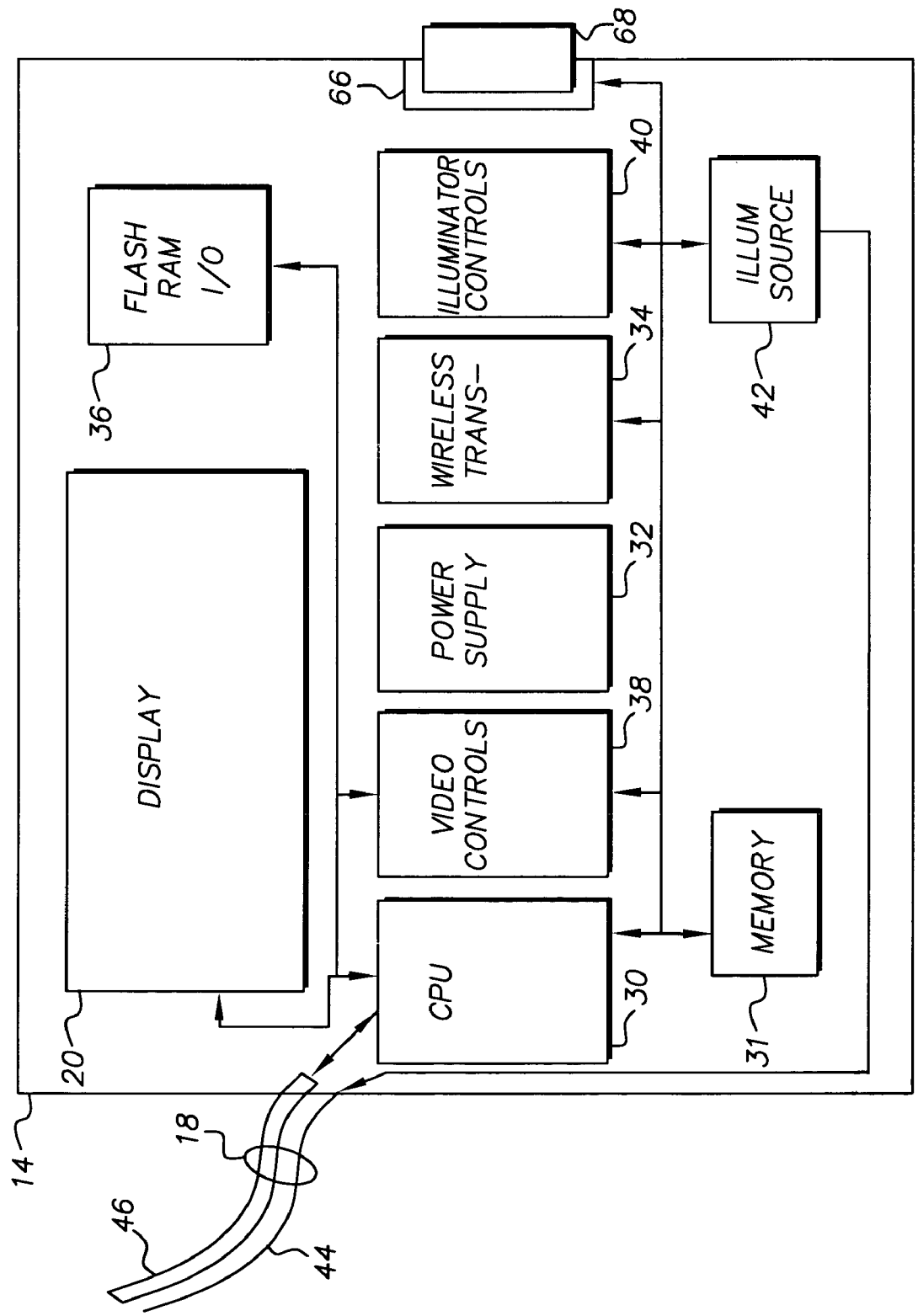
FIG. 2 shows a block diagram of the electronics in the integral base.

Referring to FIG. 2, the integral base 14 further includes a central processing unit (CPU) 30, a CPU memory 31, a power supply 32, a wireless transceiver 34, and flash memory (RAM) 36. The user controls 22 interface with a video control unit 38 and an illuminator control unit 40. The illuminator control unit 40 connects with an illumination source 42, which provides illumination to the handpiece 16 through a fiber optic 44 that is part of the cable 18. The illumination source may take a variety of forms known to those of skill in this art, such as a halogen arc lamp lighting system or a tungsten/halogen lamp. The power supply 32 is connected by a power cable (not shown) to a power source, such as a wall socket. The image signal communication between the handpiece 16 and the CPU 30 is maintained through an electrical connection 46, which is also in the cable 18. While not shown in detail, the handpiece 16 also supports a connection of the fiber optic 44 with the light emitting apertures 28 and a connection of the electrical conductor 46 to an image sensor 50, such as a conventional charge coupled device (CCD). The image sensor 50 is arranged in a conventional optical path, with mirrors and other optical components as might be necessary, such that the lens 26 can form an image of an intra-oral object on the image sensor 50.

It should be noted that portability is facilitated by incorporating into the dental camera system 10 both a high quality image display 20 along with means to transfer image data to a physically separate and distinct data storage associated with an image printing capability. The high quality image display may be provided by a number of well-known technologies; for example, it is well-known in the art of hand-held televisions (e.g., the Casio EV660 Color Active Matrix Handheld TV) to use a small (e.g., 3 inch) screen with thin-film transistor active matrix (TFT) technology. The means to accommodate a transfer of image data may include (a) wireless RF or microwave transceiver technology, (b) wireless infra-red transmission technology, and/or (c) removable memory technology embodied in physically small elements, such as flash RAM cards or small hard drives, that are easily removed from the camera part of the system and subsequently plugged into either the image data storage or printer parts of the system.

Figure 3:
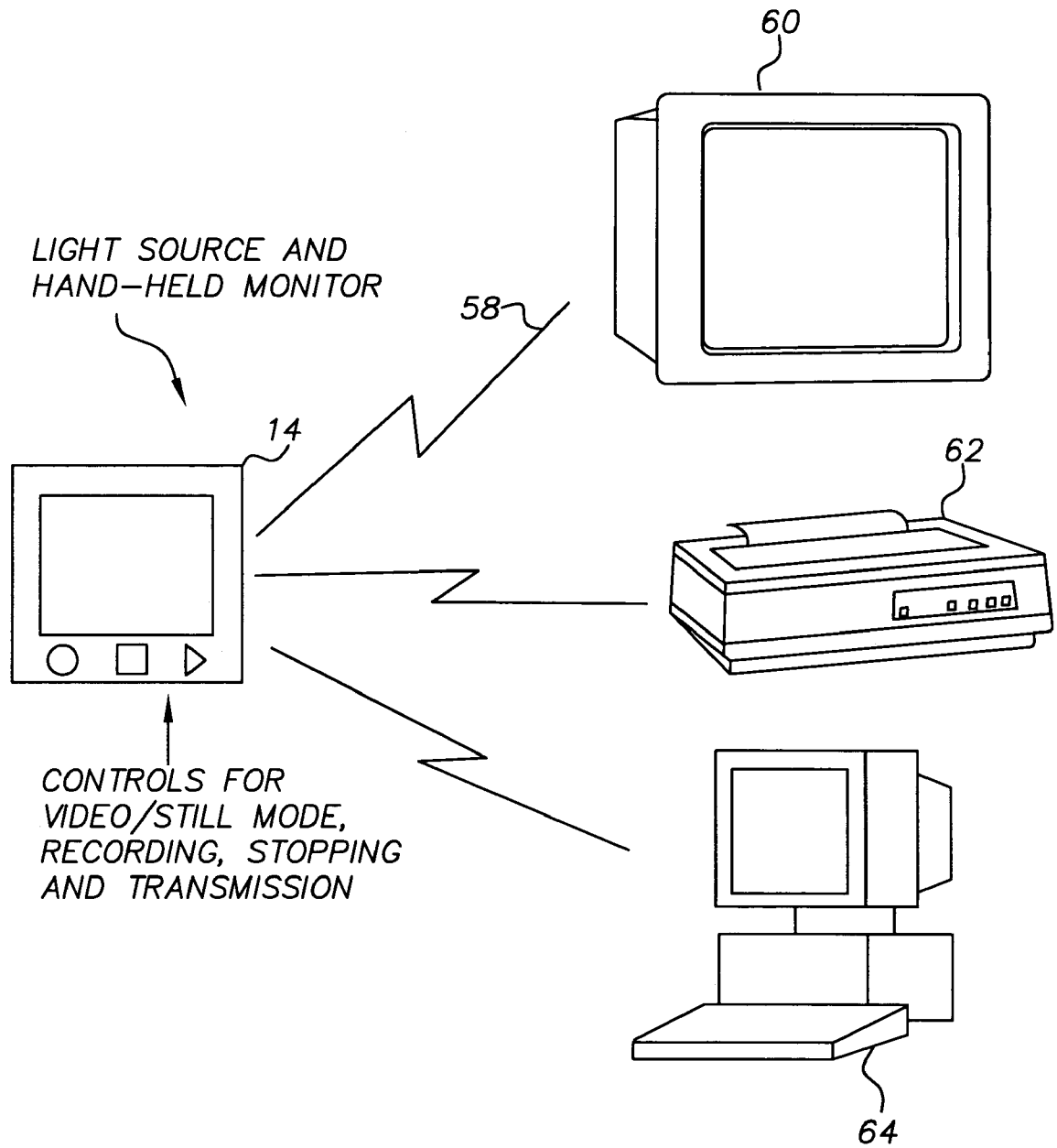
FIG. 3 shows the integral base for the light source and hand held monitor of the system shown in FIG. 1, particularly as it would be used for wireless communication to a group of peripherals.

Accordingly, the dental camera system 10 can, through the transceiver 34 in its integral base 14, initiate communication via wireless links 58 with a variety of peripheral units as shown in FIG. 3. Each of these units would have its own data storage for receiving the transmitted images. Without intending to be exhaustive as to type of peripheral unit that may be accessed, such peripheral units include a larger monitor or television receiver 60, a printer 62, and a computer system 64, such as any conventional desktop PC, where the images may be stored. With this arrangement, a dental practitioner may view an image on the integral base 14 and immediately initiate its transfer to any one of the peripheral units 60, 62 or 64 by means of the user controls 22. The incorporation of the transceiver 34 and the display monitor 20 into the dental camera system 10 further enables the practitioner to view the results of an image recording, and conveniently display the captured image(s) either for the practitioner's or patient's benefit. For this purpose, the transceiver 34 would receive images from a storage peripheral, such as the computer system 64, and display the stored images on the display monitor 20. Importantly, such viewing occurs without the requirement of producing a physical print of the image.

Just as importantly, with this arrangement the practitioner can separate the movable, but clumsy and sometimes bulky, printing and processing operation from the dental operatory, and devote a particular room to these peripherals. Moreover, incorporation of the display as a tethered adjunct to the camera system removes the requirement on the dentist to move a large bulky system (a video monitor and/or attached computer) from one operating room to the next. Alternatively, the requirement that the dentist purchase multiple such systems for multiple operatories is eliminated.

In a preferred embodiment, the image sensor 50 provides an image signal that the CPU 30 processes (as a video signal) for display on the display monitor 20. The video control unit 38 interacts through the CPU 30 and the user controls 22 to provide functionality for several modes, including a video/still mode, a mode for initiating a recording of a still or video sequence, a mode for stopping the imagery at any point (freeze-frame), a mode for initiating transmission to any of the peripherals shown in FIG. 3 and a mode for initiating retrieval of a stored image from an external memory, e.g., from the computer system 64. In the latter two modes, the images are transmitted and/or received via an antenna or light beam emitter (not shown) to/from any of the peripherals 60, 62 or 64. Alternatively, the images may be stored in a removable memory and the removable memory is then transported to the peripheral units. For instance, the integral base 14 may also include a receptacle 66 for a physically small RAM card 68, which may be easily removed from the integral base 14 and subsequently plugged into a corresponding receptacle (not shown) in any one of the peripheral units 60, 62 and 64.

Figure 4:
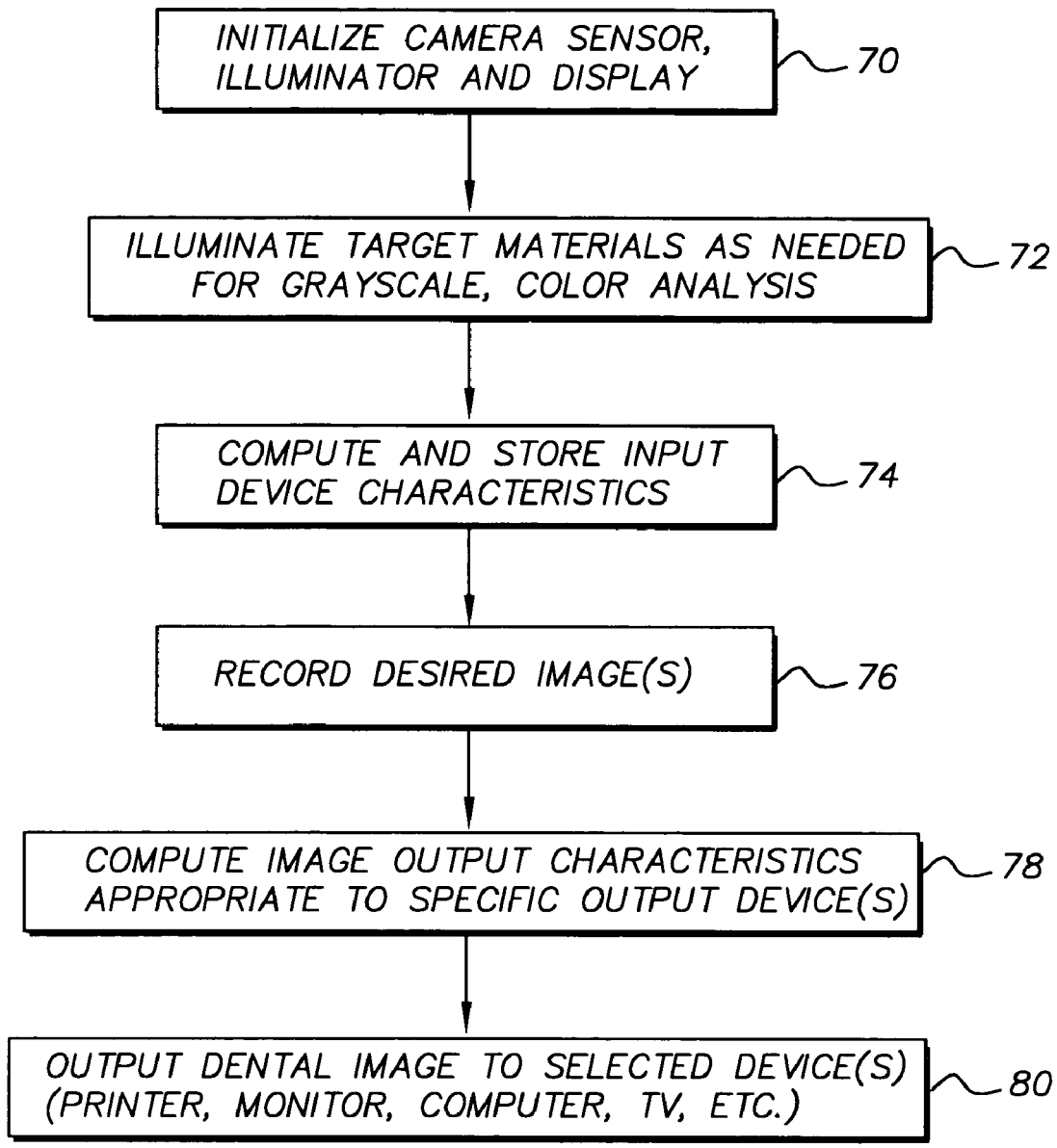
FIG. 4 shows a flow chart for a process for correcting the color of the system shown in FIG. 1.

In order to adjust the colorimetry of the dental camera system 10 to match the color of intra-oral objects, e.g., to match a natural tooth color, it is desirable to provide an optimum color calibration for an intra-oral camera application. FIG. 4 shows the process for correcting the color of a system designed for the collection of intra-oral images. It is desirable to have a broadband match (broadband spectrum) because of the need to match teeth under a variety of illumination conditions. The camera is first initialized in a stage 70 to clear previous color correction factors from the CPU memory 31. These can be in the form of look up table elements, matrix elements, and the like. As is well-known in the color management arts, these digital data are used in a mathematical transformation process to modify the color characteristics of components of the system to allow for a true color rendition to occur throughout the system. The illuminator is allowed to stabilize for a period of time so that the spectral output of the illumination source 42 remains the same for a period of time that allows multiple images to be captured, without the need for adjustment of the illuminator color temperature (or spectral output characteristics). The display monitor 20 may also require a period of stabilization before use.

In stage 72, target materials are illuminated with the illumination source 42 so as to characterize the image recording response. Such target materials can include, but are not limited to, color matching charts for the fabrication of color-matched prostheses. For example, the target materials would include the white(s) that dental practitioners use to match teeth for prosthetic purposes, such as the fabrication of a crown. (Note that calibration would ordinarily not be done with the intra-oral camera in a patient's mouth; the camera would typically be hooked up to the computer 64 for this calibration process.) Calibration of the system includes measurements of such targets to establish the characteristic input color response for the intra-oral camera system. The characteristic is stored digitally in stage 74 in the CPU memory 31 and used to transform the unknown color of the teeth (which are imaged in a separate image recording event or events resulting from stage 76) to a color representation within the system that can be used to produce a "true-color" output. The calibration of each output device is also performed and stored in stage 78 in the respective memories (not shown) of each output device. Then, the dental image is output to a selected output device(s) in stage 80, e.g., to the display monitor 20 or any of the output devices 60, 62 and 64 shown in FIG. 3. In this manner, the system can correct for color imbalance in any of the components in the system and render color corrected output regardless of the output channel.

Figure 5:
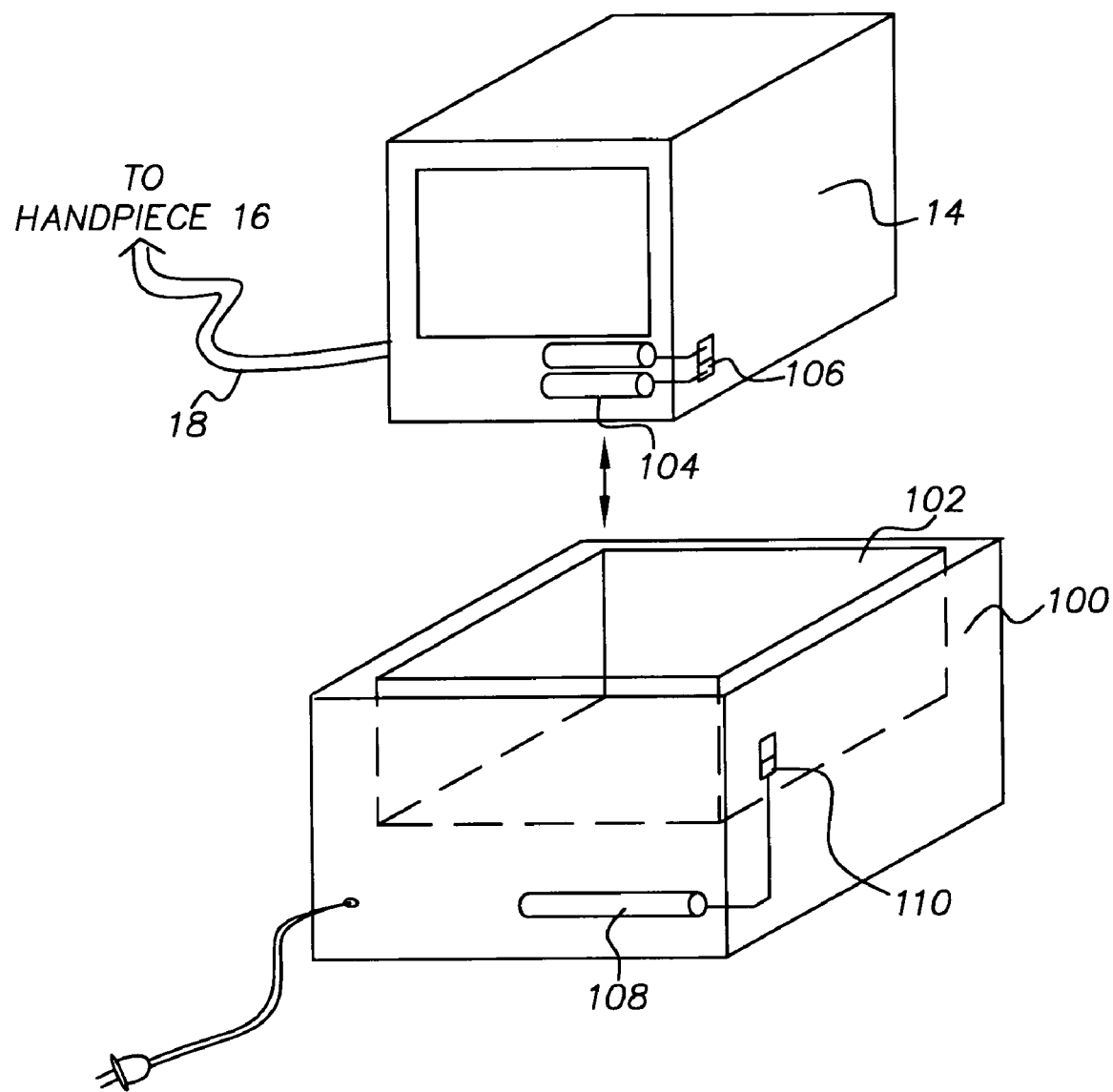
FIG. 5 shows a second embodiment of an intra-oral camera and display system according to the invention.

In a second embodiment of the invention shown in FIG. 5, the intra-oral camera and display system includes a docking unit 100 with a recessed area 102 for mating with the integral base 14. The power supply 32 in the integral base 14 includes rechargeable batteries 104 connected to externally accessible charging electrodes 106. The docking unit 100 is provided with a battery charger 108 connected to externally accessible charging electrodes 110. When the integral base 14 is inserted into the recessed area 102 on the docking unit 100, the electrodes 106 and 110 are electrically connected and the batteries 104 are recharged.

Figure 6:
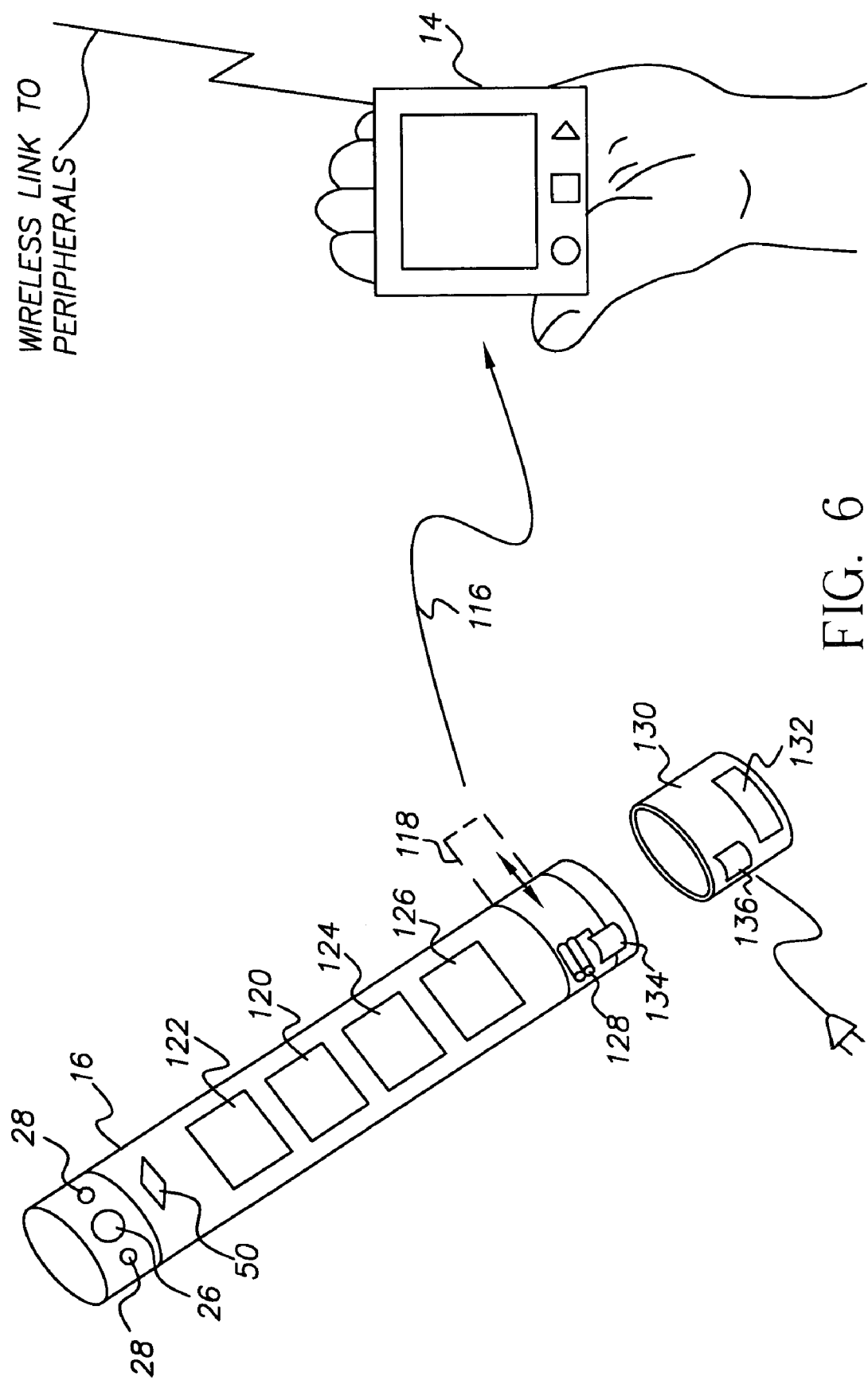
FIG. 6 shows a third embodiment of an intra-oral camera and display system according to the invention.

In a third embodiment of the invention shown in FIG. 6, the handpiece 16 of the intra-oral camera and display system includes electronics and an interface for communicating with the integral base 14 across a wireless transmission linkage 116 or by means of a removable memory 118. More specifically, the handpiece 16 includes its own light source 120, processor 122, transceiver 124 and power supply 126. In addition, the power supply 126 may include rechargeable batteries 128, and the intra-oral camera and display system can further include a docking unit 130 with a battery charger 132. Both the handpiece 16 and the docking unit include mating electrodes 134 and 136 such that when the handpiece 16 is inserted into the docking unit 130, the electrodes 134 and 136 are electrically connected and the batteries 128 are recharged. In addition, as shown in FIG. 5, the integral base may have its own docking unit; moreover, the two docking units could be combined in one component.

The invention has been described with reference to a preferred embodiment. However, it will be appreciated that variations and modifications can be effected by a person of ordinary skill in the art without departing from the scope of the invention.

PARTS LIST

10 dental camera system
12 portable dental camera
14 integral base
16 handpiece
18 cable
20 display monitor
22 user controls
24 removable lens unit
26 lens
28 light emitting apertures
30 CPU
31 CPU memory
32 power supply
34 wireless transceiver
36 flash memory
38 video control unit
40 illuminator control unit
42 illumination source
44 fiber optic
46 electrical conductor
50 image sensor
58 wireless link
60 larger monitor or television receiver
62 printer
64 computer system
66 receptacle
68 RAM card
70 initialize stage
72 illuminate target stage
74 compute stage
76 record stage 78 output compute stage
80 output select stage
100 docking unit
102 recessed area
104 rechargeable batteries
106 charging electrodes
108 battery charger
110 charging electrodes
116 wireless link
118 removable memory card
120 light source
122 processor
124 transceiver
126 power supply
128 rechargeable batteries
130 docking unit
132 battery charger
134 electrodes
136 electrodes

What is claimed is:

1. A portable intra-oral capture and display system, said system comprising:

a handpiece elongated for insertion into an oral cavity, said handpiece including a light emitter on a distal end thereof for illuminating an intra-oral object in the cavity and an image sensor for capturing an image of the intra-oral object and generating an image signal therefrom;

a portable, hand-cradled base flexibly tethered to the handpiece such that the base may be hand positioned relative to a user's line of sight without moving the handpiece, said base containing in a single integral enclosure a light source for generating light, electronics for processing the image of the intra-oral object for display, a display monitor for displaying the image of the intra-oral object, a storage for storing the image of the intra-oral object, thereby providing a stored image of the intra-oral object for subsequent review and access, and an interface for transferring the stored image of the intra-oral object to a peripheral device;

wherein the base further includes interface electronics for transferring the stored image to the peripheral device through the interface, retrieving one or more stored images from the peripheral device through the interface and displaying the retrieved stored images on the display monitor, and a set of user controls for allowing the user to enable the interface electronics to transfer the stored image to the peripheral device and to retrieve the one or more stored images from the peripheral device; and an optical connection for transmitting the light from the base to the light emitter in the camera, and an electrical connection for communicating the image signal from the image sensor in the camera to the electronics in the base.

2. The intra-oral capture and display system as claimed in claim 1 wherein the optical and electrical connections are bundled in a single cable that tethers the base to the handpiece.

3. The intra-oral capture and display system as claimed in claim 1 wherein the image displayed is a motion image.

4. The intra-oral capture and display system as claimed in claim 1 wherein the image displayed is a still image.

5. The intra-oral capture and display system as claimed in claim 1 wherein the electronics includes user controls for manipulating the image on the display.

6. The intra-oral capture and display system as claimed in claim 1 wherein the storage is a flash RAM.

7. The intra-oral capture and display system as claimed in claim 1 wherein the interface includes an electrical receptacle connected to the interface electronics for receiving a removable storage device on which the image may be stored.

8. The intra-oral capture and display system as claimed in claim 1 wherein the interface electronics includes a transceiver for initiating a wireless connection with the peripheral.

9. The intra-oral capture and display system as claimed in claim 1 wherein the peripheral includes at least one of a printer, a monitor and a computer.

10. A dental image processing system comprising:

a portable intra-oral camera and display system connected by a wireless link to one or more peripheral processing devices remote from the camera and display system;

wherein said portable camera and display system comprises:

a handpiece elongated for insertion into an oral cavity, said handpiece including a light emitter on a distal end thereof for illuminating an object in the cavity and an image sensor for capturing an image of the object and generating an image signal therefrom that is calibrated for the colorimetry of the camera and display system;

a portable, hand-cradled base containing in a single integral enclosure electronics for processing the image for display, a display monitor for displaying the image and a wireless device for establishing the wireless link and transmitting the image from the base to one or more peripheral devices located remote from the intra-oral capture and display system;

a connection for communicating the image signal from the image sensor in the camera to the electronics in the base, where the connection allows the handpiece and the base to be independently movable with respect to each other; and wherein the dental image processing system provides color calibration across the entire dental image processing system, whereby the handpiece is used to illuminate target materials to characterize a characteristic input color response of the portable intra-oral camera and display system and whereby the color calibration further includes characterization of a characteristic color response of one or more output devices, including one or more of the peripheral devices that render the image.

11. The dental image processing system as claimed in claim 10 wherein the connection is a cable, and the base includes a light source for generating light and the cable further includes an optical connection for transmitting the light from the base to the light emitter in the handpiece.

12. The dental image processing system as claimed in claim 10 wherein the peripheral processing device includes at least one of a printer, a monitor and a computer.

13. The dental image processing system as claimed in claim 10 wherein said wireless device is a wireless RF transmitter.

14. The dental image processing system as claimed in claim 10 wherein said wireless device is an infra-red transmitter.

15. The dental image processing system as claimed in claim 10 wherein the wireless device further includes the capability of receiving an image from one or more of the peripheral devices.

16. The dental processing system as claimed in claim 10 wherein the target materials include color matching charts for tooth color.

17. A portable intra-oral capture and display system, said system comprising:
- a handpiece elongated for insertion into an oral cavity, said handpiece including a light emitter on a distal end thereof for illuminating an object in the cavity and an image sensor for capturing an image of the object and generating an image signal therefrom, said handpiece including a light source for generating light for the light emitter, electronics for processing the image signal, an interface for transferring the image signal from the handpiece and a first rechargeable power supply for powering the handpiece;
- a portable, hand-cradled base containing in a single integral enclosure an interface for receiving the image signal from the handpiece, electronics for processing the image signal for display, a display monitor for displaying the image signal, and a second rechargeable power supply for powering the base; and
- a docking stage for receiving the handpiece and the base, said docking stage having one or more rechargers for recharging the power supply in the handpiece or the base when the handpiece or the base is received into the docking stage.

18. The intra-oral capture and display system as claimed in claim 17 wherein the interface includes a removable storage device on which the image may be stored.

19. The intra-oral capture and display system as claimed in claim 17 wherein the interface includes a transceiver for initiating a wireless connection with the base.

20. The intra-oral capture and display system as claimed in claim 17 wherein the power supplies in the handpiece and base further include rechargeable batteries and the docking stage further includes a first docking unit for receiving the handpiece, said first docking unit having a battery recharger for recharging the batteries in the handpiece when the handpiece is received into the first docking unit and a second docking unit for receiving the base, said second docking unit having a battery recharger for recharging the batteries in the base when the base is received into the second docking unit.

21. A method for capturing pictorial images of the interior of a patient's mouth in order to provide a diagnosis of dental and oral disease as well as a visual record of the condition of the patient, said method comprising the steps of:
- providing a handpiece component that is elongated for insertion into the patient's mouth, said handpiece component including a light emitter on a distal end thereof for illuminating dental structure in the mouth of the patient and an image sensor for capturing an image of the dental structure and generating an image signal therefrom;
- capturing a pictorial image of the interior of the patient's mouth, including the dental structure, by placing the handpiece component in proximity to the dental structure;
- providing a hand-sized base component that is easily cradled, supported and held by one hand, said base component containing in a single integral enclosure an electronics stage for processing the image of the dental structure for display, a display monitor for displaying the image of the dental structure, and a storage for storing the image of the dental structure, thereby providing a stored image of the dental structure for subsequent review and access;
- providing a transfer interface between the handpiece component and the base component that allows each component to be independently movable with respect to the other component, said transfer interface being adapted to transfer the image of the dental structure between the handpiece component and the base component;
- transferring the pictorial image of the dental structure from the handpiece component to the base component over the transfer interface;
- displaying the pictorial image of the dental structure on the display monitor of the base component; and
- manipulating the hand-sized base component relative to the handpiece component such that one person may capture the pictorial image of the dental structure with the handpiece component held in one hand while positioning the base component in the other hand for best viewing of the displayed image.

22. The method as claimed in claim 21 wherein the transfer interface is a cable connection between the handpiece component and the base component.

23. The method as claimed in claim 21 wherein the transfer interface is a wireless connection between the handpiece component and the base component.

24. The method as claimed in claim 23 wherein the wireless connection is an RF connection.

25. The method as claimed in claim 23 wherein the wireless connection is an infra-red connection.

* * * * *